(12) United States Patent
Feuerlein

(10) Patent No.: US 7,995,811 B2
(45) Date of Patent: Aug. 9, 2011

(54) METHOD FOR AN IMAGING DEVICE FOR ANATOMICALLY ASSIGNING AN IMAGE GENERATED BY THE IMAGING DEVICE, AND A COMPUTER PROGRAM PRODUCT THAT IS SET UP FOR CARRYING OUT SUCH A METHOD

(75) Inventor: Ute Feuerlein, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 963 days.

(21) Appl. No.: 11/498,850

(22) Filed: Aug. 4, 2006

(65) Prior Publication Data

US 2007/0030346 A1    Feb. 8, 2007

(30) Foreign Application Priority Data

Aug. 5, 2005   (DE) .................... 10 2005 037 019

(51) Int. Cl.
  *G06K 9/00* (2006.01)
  *G06K 9/46* (2006.01)
  *G06K 9/62* (2006.01)
  *G06K 9/36* (2006.01)
  *G06K 9/32* (2006.01)
  *A61B 1/04* (2006.01)
  *A61B 5/05* (2006.01)

(52) U.S. Cl. ........ 382/128; 382/131; 382/203; 382/209; 382/291; 382/294; 600/125; 600/407

(58) Field of Classification Search ................ 378/1–90; 382/128, 130, 131, 164, 162, 165, 168–173, 382/180, 209, 215–218, 224–225
See application file for complete search history.

(56) References Cited

U.S. PATENT DOCUMENTS

| | | | | |
|---|---|---|---|---|
| 5,267,296 | A * | 11/1993 | Albert | 378/113 |
| 5,673,298 | A * | 9/1997 | Mazess | 378/54 |
| 2004/0101175 | A1* | 5/2004 | Yarger et al. | 382/128 |
| 2006/0120583 | A1* | 6/2006 | Dewaele | 382/128 |

OTHER PUBLICATIONS

Hahn et al., "Verification of Lumbosacral Segments on MR Images: Identification of Transitional Vertebrae", Radiology, 1992, vol. 182, pp. 580-581.*

(Continued)

*Primary Examiner* — Tom Y Lu
*Assistant Examiner* — Thomas A Conway
(74) *Attorney, Agent, or Firm* — Harness, Dickey & Pierce, PLC

(57) ABSTRACT

A method is disclosed for an imaging device, for anatomically assigning an image generated by the imaging device to object components of an object. Further, a computer program product and computer readable medium are disclosed, which are set up to carry out such a method. In the method, the object components are identified in a substantially autonomous fashion in an overview image that covers a larger area than an examination area. The image of the examination area is automatically assigned to at least one object component identified in the overview image given a known positional relationship between the image and the overview image, such that there is no need for an operator to carry out an individual assignment of the imaged object components.

18 Claims, 4 Drawing Sheets

OTHER PUBLICATIONS

Guld, M. O. Kohnen, M. Keysers, D. Schubert, H. Wein, B. B.; Bredno, J. Lehmann, T. M. "Quality of DICOM header information for image categorization"; International Society for Optical Engineering (Proceedings—SPIE the International Society for Optical Engineering); 1999; 2002, ISSU 4685, pp. 280-287.

German Search Report dated Mar. 20, 2007.

A new accurate and precise 3-D segmentation method for skeletal structures in volumetric CT Data (Kang, Y., Engelke, K.; Kalender, W.) 2003, IEEE Medical Imaging 2006Q13650.

Carballido-Gamio, Julio; Belongie, Serge J.; Majumdar.Sharmila: "Normalized Cuts in 3-D for Spinal MRI Segmentation", 2004, IEEE Trans. on Medical Imaging, vol. 23 (1), pp. 36-44, ISSN: 0278-0062, DOI: 10.1109/TMI.2003.819929; Others.

Deschenes, S.; Guise, J.: "Wavelet-Based Automatic Segmentation of the Vertebral Bodies in Digital Radiographs", 2002, IEEE Acoustics, Speech, and Signal Processing (ICASSP'02), vol. 4, pp. 3868-3871, ISSN: 1520-6149, DOI: 10.1109/ICASSP.2 002.1004762; Others.

* cited by examiner

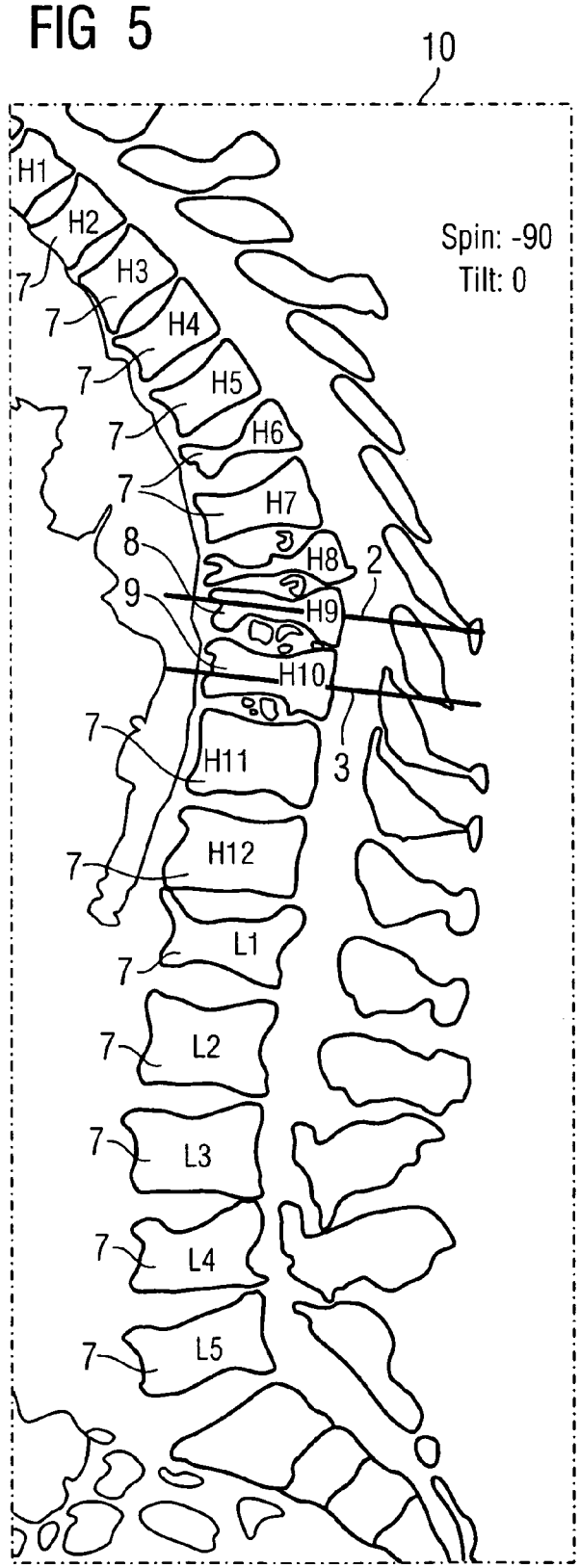
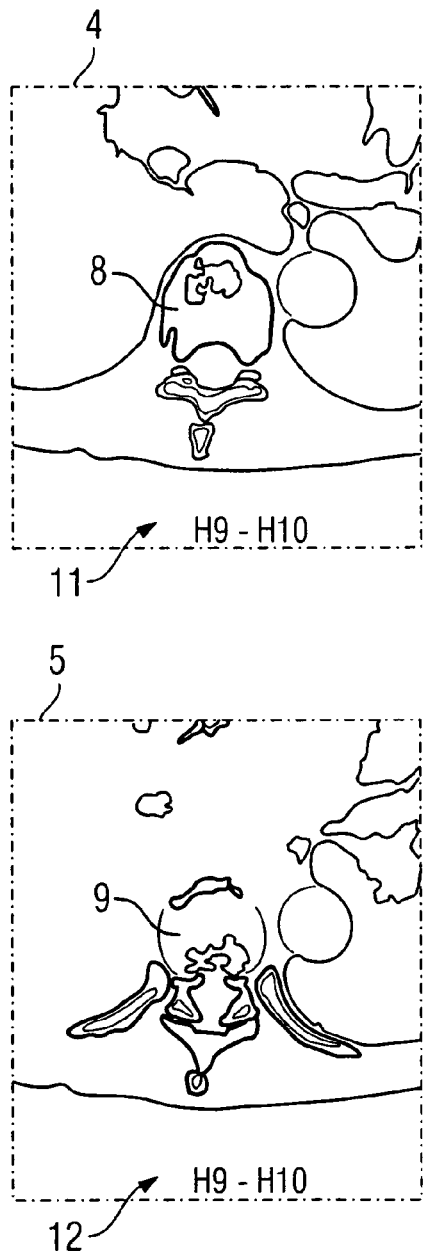

METHOD FOR AN IMAGING DEVICE FOR ANATOMICALLY ASSIGNING AN IMAGE GENERATED BY THE IMAGING DEVICE, AND A COMPUTER PROGRAM PRODUCT THAT IS SET UP FOR CARRYING OUT SUCH A METHOD

PRIORITY STATEMENT

The present application hereby claims priority under 35 U.S.C. §119 on German patent application number DE 10 2005 037 019.5 filed Aug. 5, 2005, the entire contents of which is hereby incorporated herein by reference.

FIELD

The invention generally relates to method for an imaging device, for example to one for anatomically assigning an image generated by the imaging device. Further, it generally relates to a computer program product that is set up for carrying out such a method.

BACKGROUND

When examining an object in the case of which an image generated by an imaging device is evaluated, the treating doctor must know which component of the object is displayed in the image.

Thus, during the examination of, for example, vertebral bodies of a patient it is necessary to assign an image, generated by a computed tomography device or by a magnetic resonance device, in the form of a slice image or volume image to that vertebral body of the patient being imaged in the image. Such an assignment is possible only with great difficulty solely on the basis of the image in which the examination area is shown in detail. The assignment between the vertebral bodies and the image is therefore generally performed with the assistance of an overview image in which a much larger anatomical context of the examination area can be seen.

Such overview images are generated in the form of topograms in the case of an imaging device in the form of a computed tomography device. The assignment of a vertebral body to the image is performed by virtue of the fact that all the vertebral bodies are firstly identified in the overview image by a visual consideration of the anatomical context. The operator subsequently transmits the information relating to the identified vertebral body into a comments field in the generated image.

Because there is a high risk of vertebral bodies being confused, it is necessary for the purpose of unambiguous identification in the topogram always to have the first cervical vertebral body or the last lumbar vertebral body depicted in the topogram such that it is possible to number the vertebral bodies. If the topogram is not stored with the image or is changed, for example owing to a change in the image resolution or a change in the image section, it is no longer possible to assign the image reliably to a vertebral body.

SUMMARY

A precondition for an imaging device is provided, in at least one embodiment, that can be used to provide that an image generated by the imaging device is reliably assigned anatomically in a simple way to an object component.

The inventor has realized that it is a complicated matter to assign an image generated by an imaging device, for example a slice image or volume image generated by a computed tomography device or a magnetic resonance device, to an object component of an object, for example to a vertebral body of a patient, in the case of which a visual identification of the object components is undertaken in an overview image and the object components are marked by hand, the information about the object components imaged in the image being transmitted into the image, and that it entails the risk of wrongly assigning the image.

In order to avoid or lessen at least one of such disadvantages, at least one embodiment of the invention proposes a method for an imaging device for anatomically assigning an image generated by the imaging device and in which an examination area of an object is imaged, to object components of the object, in which (a) an overview image is generated, the overview image covering an area that is larger than the examination area of the object, (b) object components in the generated overview image are identified in substantially autonomous fashion, (c) the image of the examination area is automatically assigned to at least one object component identified in the overview image given a known positional relationship between the image and the overview image.

Wrong assignments by an operator are largely avoided on the basis of the substantially autonomous identification of object components and the automatic assignment of the image to the object component imaged in the image.

An item of information relating to the object component assigned to the image is preferably stored together with the image such that once an assignment has been made the information is also available without evaluating the overview image or in the event of a change in the resolution or in the section of the overview image, for subsequent reformations, for example when reprocessing the generated image or during osteoporosis measurements. Moreover, it can likewise be advantageous to store an information item relating to the object components identified in the overview image together with the overview image.

The object components are advantageously identified autonomously in the generated overview image with the aid of methods of digital image processing such that very differently shaped object components can be identified in a simple way by an appropriate matching of digital image filters. In an advantageous refinement of an embodiment of the invention, the image processing comprises an evaluation of an object geometry of the object components, for example on the basis of object contours that can easily be extracted by an evaluation of the gradients present in the image.

The image processing can likewise advantageously comprise an evaluation of the distribution, characteristic of the respective object component, of the image values, for example in a defined local neighborhood. Thus, for example, the homogeneity of the image values that is present in the local neighborhood can also be used as a feature for classifying object components.

The result of an autonomous identification of object components is advantageously improved by virtue of the fact that an operator can manually mark at least one object component such that, together with the prior knowledge relating to the anatomical context, or the positional relationship of the object components one to another, it is possible to assign the remaining object components autonomously in a reliable way.

In the simplest case, the object components can be numbered as result of the identification in accordance with the anatomy of the object. Such a procedure is appropriate, in particular, in the case of a high number of comparably designed object components such as is the case, for example, with the vertebral bodies or with the teeth.

The information relating to the identified object components can preferably be inserted or suppressed visually in the overview image. The optional insertion and suppression of the information offers the advantage that, on the one hand, in the case of inserted information the operator can acquire a quick overview of the anatomical context of the object components and, on the other hand, that no image information is lost through being overlaid in the case of suppressed information.

In an advantageous refinement of an embodiment of the invention, there is generated by the imaging device an image in the form of a slice image or volume image in the case of which individual objects are generally imaged with a high resolution but without further anatomical context. An assignment is advantageously undertaken for object components in the form of vertebral bodies or in the form of teeth for which a high risk of confusion exists because of the similar features of the object components.

The assignment of the object components can be used with a particularly low outlay for imaging devices in the form of an X-ray machine, a magnetic resonance device, an ultrasound device or else in the form of a positron emission tomography device, since in the case of the above devices all the hardware components required for the method, for example an arithmetic logic unit for evaluating the overview image, are already present as a rule.

It can likewise be advantageous to carry out the assignment for a multimode device in the case of which images of object components are generated by different devices.

The overview image in which all the relevant information relating to the anatomical context is included, can be generated in a particularly simple and quick fashion in the form of a topogram when use is made of a computed tomography device.

BRIEF DESCRIPTION OF THE DRAWINGS

Example embodiments of the invention and further advantageous refinements of the invention are illustrated in the following schematics, in which:

FIG. 5 shows a result of the anatomical assignment of the image to the corresponding object component in pictorial form.

DETAILED DESCRIPTION OF THE EXAMPLE EMBODIMENTS

Figure 1:
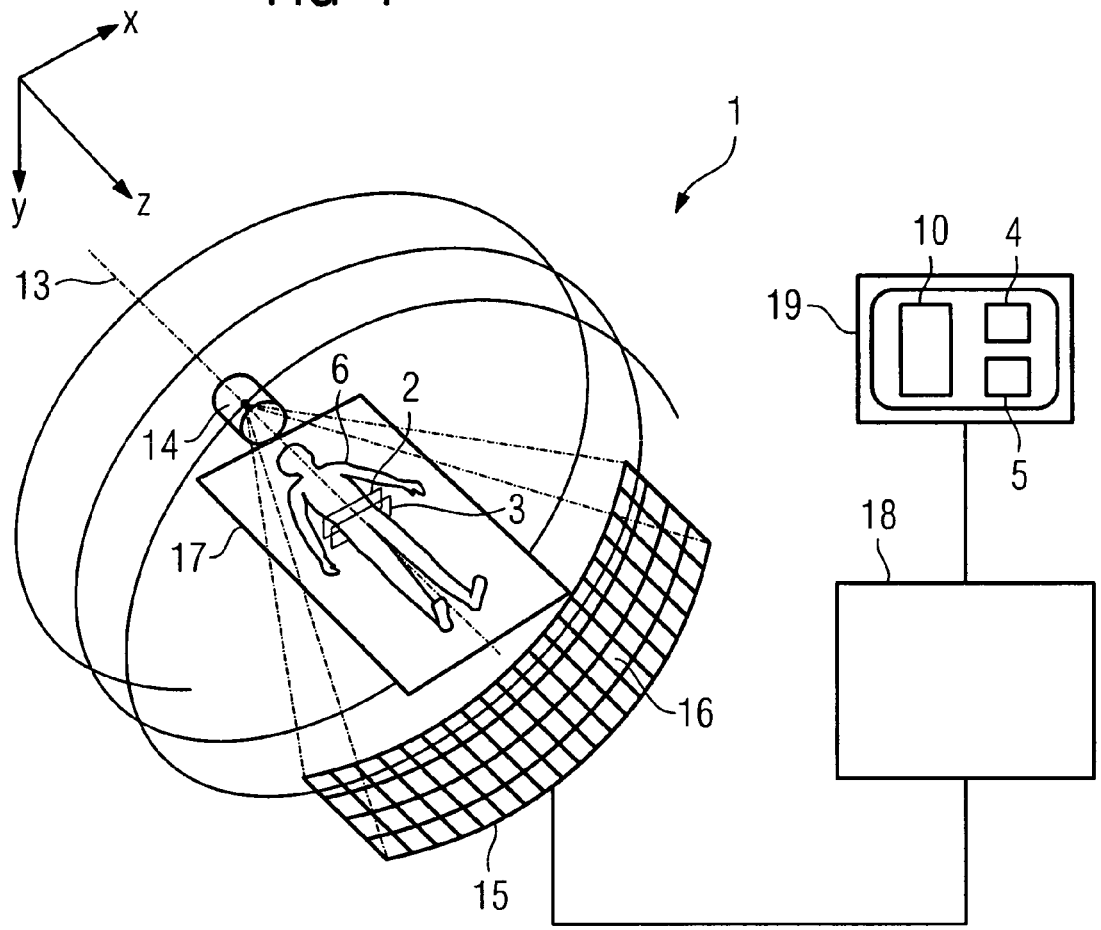
FIG. 1 shows an imaging device that is suitable for carrying out the method according to an embodiment of the invention for anatomically assigning an image generated by the imaging device, in a perspective view.

FIG. 1 shows an imaging device, here a computed tomography device provided with the reference numeral 1, in a perspective view that is suitable for carrying out the method according to an embodiment of the invention for anatomically assigning an image 4; 5 generated by the computed tomography device 1.

Located in the interior of the computed tomography device 1 is a recording system 14, 15 that is arranged rotatably about an axis of rotation 13 on a gantry (not illustrated) and has an emitter 14 in the form of an X-ray tube and a detector 15 arranged opposite this emitter. The detector 15 is of arcuate design and includes a number of detector elements 16 lined up to form detector rows, only one detector element being provided with a reference numeral.

An X radiation generated by the emitter 14 penetrates a measuring area and subsequently strikes the detector elements 16 of the detector 15. The detector elements 16 in this case generate attenuation values dependent on the attenuation of the X radiation. The conversion of the X radiation into an attenuation value is performed, for example, by means in each case of a photodiode optically coupled to a scintillator, or by means of a directly converting semiconductor. The detector 15 in this way generates a set of attenuation values that is also denoted as a projection.

The computed tomography device 1 is assigned a support device with a movable table top 17 on which an object, for example a patient provided with the reference numeral 6, can be supported. The table top 17 is arranged adjustably in the direction of the axis of rotation 13.

The computed tomography device 1 can be operated in different operating modes. In the case of generation of an overview image 10, projections are acquired in conjunction with continuous advancing of the patient 6 in the direction of the axis of rotation 13, but with a permanently set rotary angle position of the recording system 14, 15. It is thereby possible, for example, for a lateral image of the patient 6 to be displayed in the overview image 10 such that a large anatomical context of an examination area 2; 3 is imaged in the image 4; 5.

When generating a slice image or volume image, the projections are obtained in contrast thereto from a multiplicity of different projection directions in conjunction with simultaneous rotation of the recording system 14, 15 about the axis of rotation 13. The scanning can be performed in this case with or without advancing the patient 6 in the direction of the axis of rotation 13.

The projections of the recording system 14, 15 that are obtained during scanning are transmitted to an arithmetic logic unit 18 where they are converted into the image 4; 5 by calculation and are evaluated with the aid of methods of digital image processing. The calculated image 4; 5 includes image values, each image value representing a gray-scale value dependent on the attenuation. It is possible for intermediate and result images of the calculation to be displayed on a display unit 19.

Figure 2:
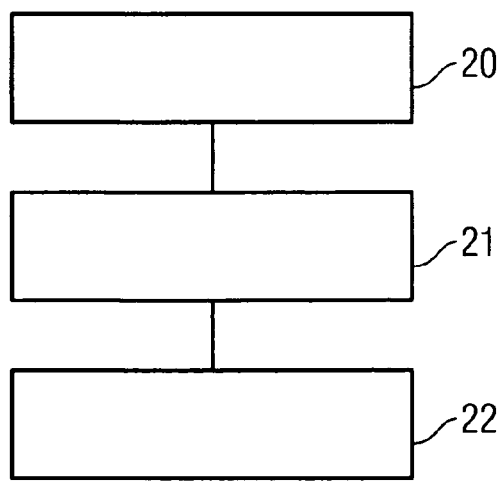
FIG. 2 shows a sequence of the method according to an embodiment of the invention for anatomically assigning an image generated by the imaging device, in an outlined form.

FIG. 2 illustrates schematically a sequence of the method according to the invention for anatomically assigning an image 4; 5 generated by the imaging device 1 to object components 7, 8, 9 of an object 6. The overview image 10 is generated in a method step 20, the overview image 10 covering an area that is larger than the examination area 2; 3 of the object. The computed tomography device 1 typically generates as overview image 10 a topogram in which, for example, a lateral image of the patient 6 with all the object components 7, 8, 9 in the form of vertebral bodies can be seen.

Subsequently, the object components 7, 8, 9 are identified in substantially autonomous fashion in the generated overview image 10 in a second method step 21. Methods of digital image processing are used for the autonomous identification of the object components 7, 8, 9. A gradient image in which all the contours are highlighted is, for example, calculated from the overview image 10. The gradient image is subsequently subjected to gray-scale value segmentation such that a binary image is produced. Here, a pixel of a potential edge corresponds to a set pixel in the binary image. The segmented image is subsequently examined topologically such that it is possible to identify those object components 7, 8, 9 whose contour has a profile characteristic of the component.

Moreover, the statistical distribution of gray scale values in a local neighborhood can be analyzed as an additional decision criterion for identifying purposes, so that, for example, a parameter can be calculated as a measure of the homogeneity. The parameter is comparable to the expected values of a homogeneity of the object components 7, 8, 9, and so an additional evaluation criterion is available.

In order to reduce the required computing time and for the purpose of reliable identification of the object components 7, 8, 9, an object component 7; 8; 9 is marked manually by an operator, and the autonomous identification of the remaining object components is performed starting therefrom. The identification can be performed by taking account of prior knowledge relating to the anatomical circumstances, and so it is possible to evaluate the image information in the overview image 10 in a fashion that is targeted and restricted to specific image areas.

After the identification of the object components 7, 8, 9, in a third method step 22 the generated image 4; 5 of the examination area 2; 3, which has been recorded for diagnostic aims by the computed tomography device 1 is automatically assigned to an object component 7; 8; 9 identified in the overview image 10, the positional relationship between the image 4; 5 and the overview image 10 being known.

For the purpose of a quick overview, it is an advantage for a treating person when the anatomical information of the object components 7, 8, 9 can optionally be inserted visually in the overview image 10 and/or in the image 4; 5.

Figure 3:
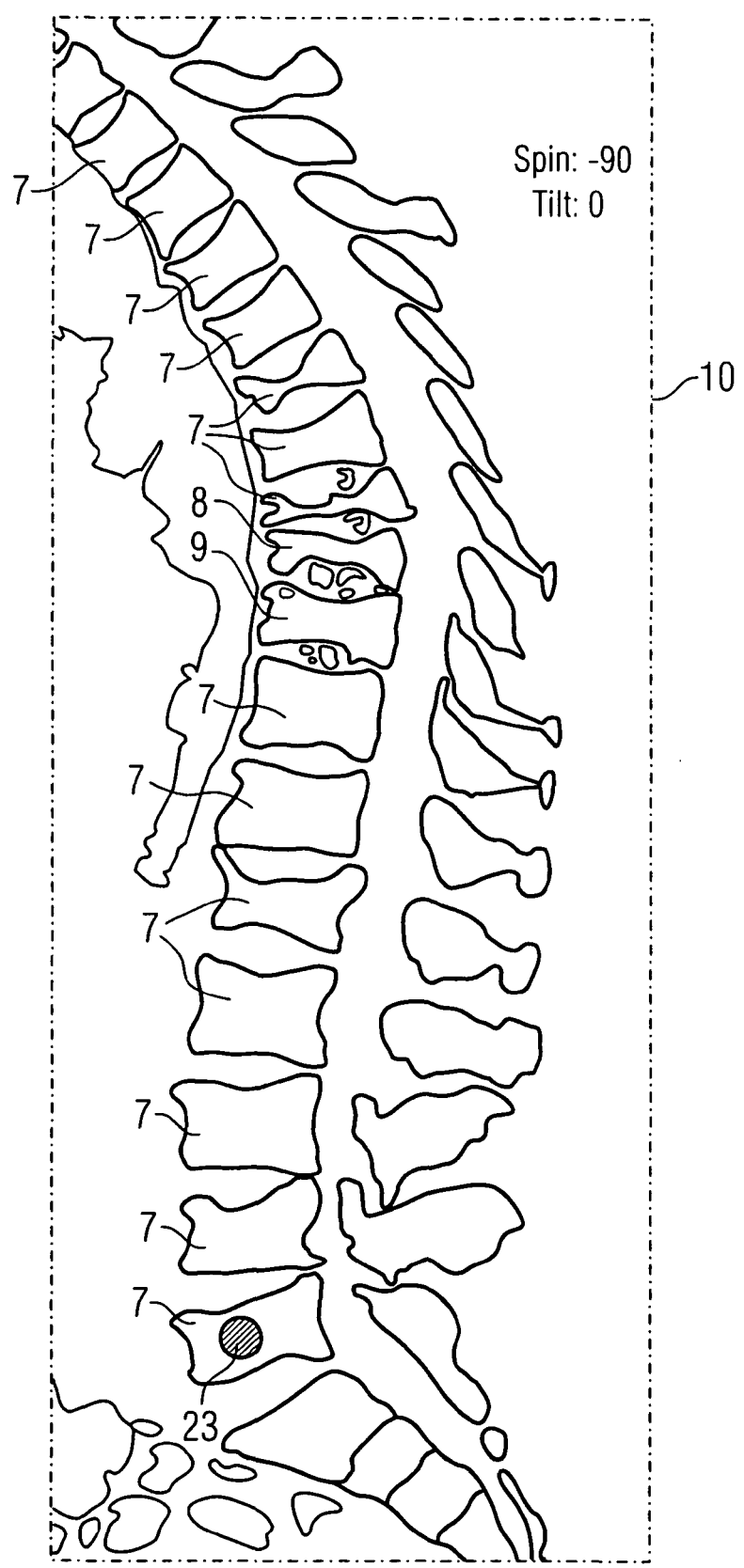
FIG. 3 shows an overview image in which object components in the form of vertebral bodies are imaged.

FIG. 3 shows the overview image 10 in the form of a topogram that has been generated by the computed tomography device 1 and shows a lateral image of a patient's spine, the object components 7, 8, 9 being represented by a number of vertebral bodies. The vertebral bodies, which represent object components, are provided below with the reference numerals 7, 8, 9, and the topogram, which represents the overview image, is provided with the reference numeral 10. Because of a similar geometrical appearance, the individual vertebral bodies 7, 8, 9 cannot, for example, be distinguished as, for example, in a slice image or volume image without the anatomical context shown in the topogram 10.

Figure 4:
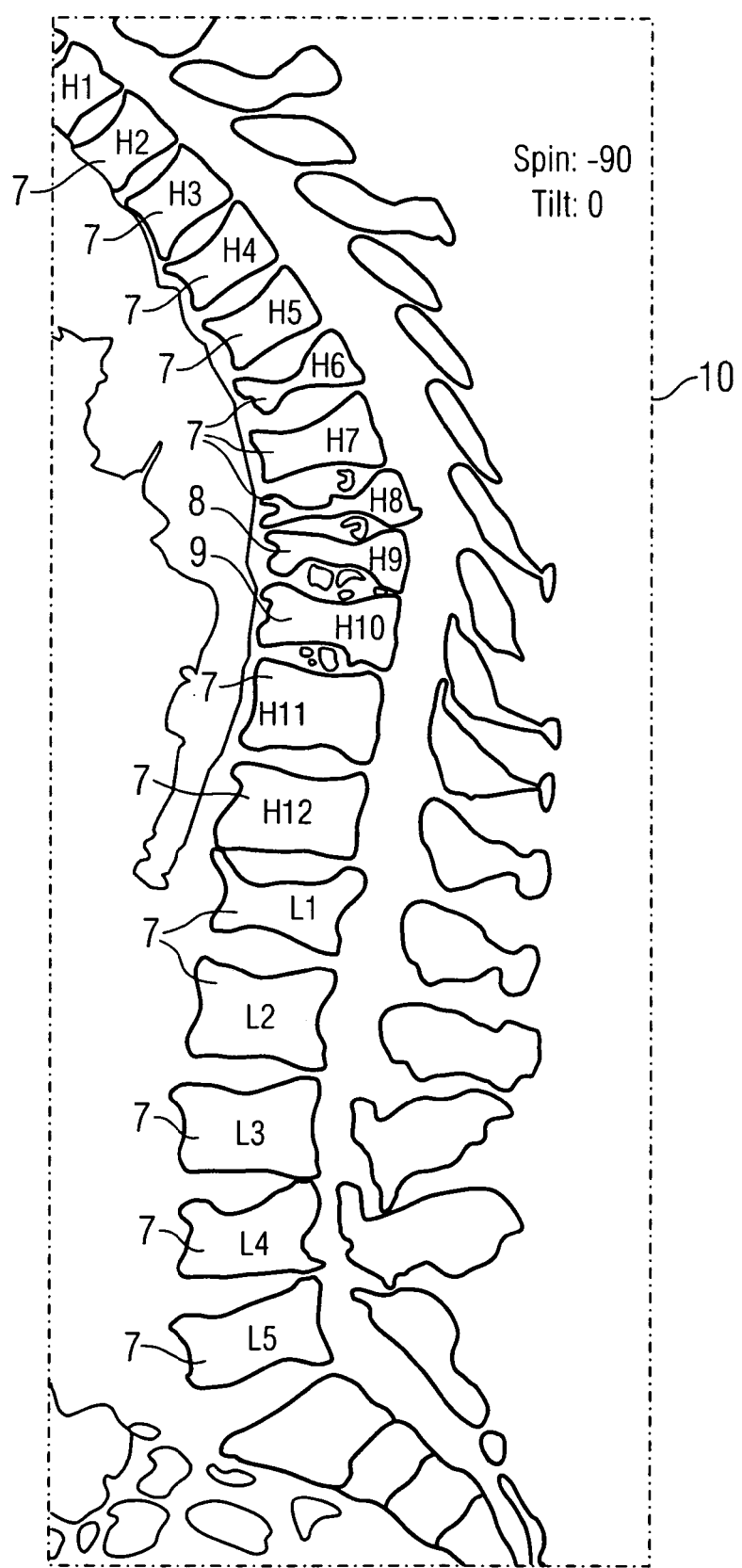
FIG. 4 shows the overview image shown in FIG. 3 and in the case of which an item of anatomical information of the identified object components is inserted visually in the overview image.

The image 4; 5 is assigned in the example in that at the start an operator uses appropriately set up operating hardware and software to mark the last lumbar vertebral body of the patient at a position 23 in topogram 10. The position 23 marked in the topogram 10 constitutes the starting point of the autonomous identification of the remaining vertebral bodies 7, 8, 9. In FIG. 4, the anatomical information of the identified vertebral bodies 7, 8, 9 is inserted visually in the topogram 10. Lumbar and dorsal vertebrae are numbered separately from one another. Lumbar vertebrae exhibit the letter L, and dorsal vertebrae the letter H at the start of a code number.

Subsequent to the identification on the vertebral bodies 7, 8, 9 the acquired image 4; 5 is assigned the object component 8; 9 imaged in the image 4; 5. FIG. 5 shows a result of the anatomical assignment of two acquired images 4; 5 in the form of slice images relating to the vertebral bodies 7, 8, 9. Illustrated on the left-hand side is the topogram 10 in which the information relating to the identified vertebral bodies 7, 8, 9 is visually inserted. Moreover, the respective examination area 2; 3 in which the image 4; 5 of the patient was acquired is depicted as a line in the topogram 10. Two of the acquired tomograms are imaged on the right-hand side. In each image 4; 5, the anatomical information 11; 12 relating to the imaged vertebral body 8; 9 is visually inserted as the result of the assignment. The result of such an assignment is stored together with the image 4; 5 such that a reliable assignment of the respective image 4; 5 is ensured even without a topogram 10.

The method described here can, however, be used not only for an imaging device in the form of a computed tomography device 1. It would likewise be conceivable to use the method for a magnetic resonance, nuclear or ultrasound device. It is also not restricted to the examination of object components in the form of vertebral bodies 7, 8, 9. It would likewise be conceivable for object components in the form, for example, of cardiac vessels or teeth to be assigned.

The essentials of the invention can be summarized as follows:

At least one embodiment of the invention relates to a method for an imaging device 1 for anatomically assigning an image 4; 5, generated by the imaging device 1, to object components 7, 8, 9 of an object 6, and to a computer program product that is set up to carry out such a method in the case of which the object components 7, 8, 9 are identified in a substantially autonomous fashion in an overview image 10 that covers a larger area than an examination area 2; 3, and in the case of which the image 4; 5 of the examination area 2; 3 is automatically assigned to at least one object component 8; 9 identified in the overview image 10, the positional relationship between the image 4; 5 and the overview image 10 being known, such that there is no need for an operator to carry out individual assignment of the imaged object components.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of an imaging device of anatomically assigning an image content of an image generated by the imaging device, the method comprising:
   generating, using the imaging device, a first image of an anatomy of an examination area of an object;
   generating, using the imaging device, an overview image, the overview image covering an area that is larger than the examination area of the object and includes a plurality of object components;
   anatomically identifying the object components in the generated overview image in an autonomous fashion without any human intervention with the aid of methods of digital image processing, the digital image processing including an evaluation of an object geometry of the object components;
   automatically assigning by anatomy and without any human intervention an image content of the first image of the examination area to at least one object component identified in the overview image based on a known positional relationship between the first image and the overview image; and
   displaying a resulting image.

2. The method as claimed in claim 1, wherein an operator manually marks at least one object component starting from which the autonomous identification of the remaining object components is performed.

3. The method as claimed in claim 1, wherein, as result of the identification of the object components, the object components are numbered in accordance with the anatomy of the object.

4. The method as claimed in claim 1, wherein an item of information relating to the object component assigned to the image content of the image is stored together with the image.

5. The method as claimed in claim 1, wherein an item of information relating to the object components identified in the overview image are stored together with the overview image.

6. The method as claimed in claim 1, wherein an item of anatomical information of the identified object component is visually inserted in the image.

7. The method as claimed in claim 1, wherein at least one of a slice image and volume image is generated as the first image by the imaging device.

8. The method as claimed in claim 1, wherein vertebral bodies are identified as object components.

9. The method as claimed in claim 1, wherein teeth are identified as object components.

10. The method as claimed in claim 1, wherein an X-ray machine is used as imaging device.

11. The method as claimed in claim 1, wherein a computed tomography unit is used as imaging device.

12. The method as claimed in claim 1, wherein a topogram is generated as overview image.

13. The method as claimed in claim 1, wherein an ultrasound device is used as imaging device.

14. The method as claimed in claim 1, wherein a magnetic resonance device is used as imaging device.

15. The method as claimed in claim 1, wherein a positron emission tomography device is used as imaging device.

16. A non-transitory computer readable medium including program segments stored thereon for, when executed on a computer, causing the computer to implement the method of claim 1.

17. The method as claimed in claim 1, wherein the methods of digital image processing comprise an evaluation of a distribution of image values of the respective object component that are present in the overview image.

18. The method as claimed in claim 17, wherein an operator manually marks at least one object component starting from which the autonomous identification of the remaining object components is performed.

* * * * *